United States Patent [19]

Lin et al.

[11] Patent Number: 4,533,742

[45] Date of Patent: Aug. 6, 1985

[54] PREPARATION OF 2-HYDROXYTETRAHYDROFURAN BY HYDROFORMYLATION OF ALLYL ALCOHOL USING KETONE SOLVENTS

[75] Inventors: Jiang-Jen Lin, Round Rock; John F. Knifton, Austin, both of Tex.

[73] Assignee: Texaco Inc., White Plains, N.Y.

[21] Appl. No.: 576,509

[22] Filed: Feb. 2, 1984

[51] Int. Cl.$^3$ .......................................... C07D 307/20
[52] U.S. Cl. .................................................. 549/475
[58] Field of Search ....................................... 549/475

[56] References Cited

U.S. PATENT DOCUMENTS

| | | | |
|---|---|---|---|
| 3,980,670 | 9/1976 | Kummer et al. | 260/343.6 |
| 4,064,145 | 12/1977 | Taylor | 260/346.11 |
| 4,083,882 | 4/1978 | Taylor et al. | 260/635 R |
| 4,139,542 | 2/1979 | Smith | 549/475 |
| 4,209,467 | 6/1980 | Kojima et al. | 260/340.7 |
| 4,356,125 | 10/1982 | de Munck et al. | 549/475 |
| 4,400,547 | 8/1983 | Dawes et al. | 568/454 |
| 4,400,548 | 8/1983 | Abatjoglou et al. | 568/454 |
| 4,400,549 | 8/1983 | Richter et al. | 568/454 |

OTHER PUBLICATIONS

Chemical Abstract 77: 139429e, 1972, Ger. Offen. 2,106,243 to Himmele, et al.
C. U. Pittman, Jr. et al., "Rhodium–Catalyzed Hydroformylation of Allyl Alcohol, a Potential Route to 1,4–Butanediol," *J. Org. Chem.* 1980, vol. 45, pp. 2132–2139.
M. Tamura, et al., "New Process for 1,4–Butanediol via Allyl Alcohol," *Chemical Economy & Engineering Review*, Sep. 1980, vol. 12, No. 9, (No. 141), pp. 32–35.
"New Applications of Carbon Monoxide Chemistry," *Research & Development Review Report* No. 19, Nippon Chemtech Consulting Inc., Mar. 1981, pp. 38–39, 42, 82.
deMunck, et al., "Gas Phase Hydroformylation of Allyl Alcohol with Supported Liquid Phase Rhodium Catalysts," *J. of Molecular Catalysis*, 11(1981), pp. 233–246.

*Primary Examiner*—Richard L. Raymond
*Attorney, Agent, or Firm*—Jack H. Park; Kenneth R. Priem; David L. Mossman

[57] ABSTRACT

A process is disclosed for preparing products such as 2-hydroxytetrahydrofuran which comprises contacting unsaturated compounds such as allyl alcohol with carbon monoxide and hydrogen in the presence of a rhodium carbonyl catalyst and a ketone solvent system. Allyl alcohol conversions of 100% and selectivities to 2-hydroxytetrahydrofuran of 96% are achievable under certain conditions. Preferred ketone solvents are acetophenone and 2-undecanone. 2-Hydroxytetrahydrofuran is an important precursor to manufacture of 1,4-butanediol.

11 Claims, No Drawings

PREPARATION OF 2-HYDROXYTETRAHYDROFURAN BY HYDROFORMYLATION OF ALLYL ALCOHOL USING KETONE SOLVENTS

BACKGROUND OF THE INVENTION

1. Field of the Invention

This invention is related to the addition of hydrogen and carbon monoxide to olefin compounds to obtain hydroxy-substituted cyclic compounds in the presence of a rhodium-containing catalyst and is more particularly related to such an addition conducted in the presence of a ketone solvent.

2. Description of Related Processes in the Field

The compound 2-hydroxytetrahydrofuran is an important intermediate for producing 1,4-butanediol. A number of unsaturated compounds to useful products.

U.S. Pat. No. 4,209,467 assigned to Daicel, Ltd. teaches a low pressure hydroformylation process in which the catalyst is a reaction product of a cobalt carbonyl compound with a nitrogen-containing heterocyclic compound having an enolic hydroxyl group on the carbon atom adjacent to the ring-forming nitrogen atom, such as 2-hydroxypyridine. Ordinarily, the pressures employed therein are in the neighborhood of 10 to 100 atmospheres. Unsaturated compounds taught as suitable for this hydroformylation process include ethylenically unsaturated hydrocarbons such as ethylene, propylene, butadiene, etc. and compounds such as allyl alcohol, allyl acetate, etc.

Closer to the invention disclosed herein are methods which involve rhodium catalysts. U.S. Pat. No. 3,980,670 discloses a process for manufacturing methacrylic acid and butyrolactone by hydroformylation of allyl esters of lower carboxylic acids in the presence of rhodium carbonyl complex catalysts followed by oxidation of the resulting formyl compounds with molecular oxygen to produce 4-acetoxy-n-butyric acid and 3-acetoxy-isobutyric acid as the major products. See also German Offen. No. 2,106,243 to BASF. Unsaturated compounds such as propylene may be hydroformylated means of rhodium/triphenylphosphine/carbonyl complexes formed in situ using a special pre-forming step described in U.S. Pat. No. 4,400,549.

Even more on point are the following patents. U.S. Pat. Nos. 4,064,145 and 4,083,882 describe a method for producing tetrahydrofuran and 1,4-butanediol by reacting synthesis gas with allyl alcohol under hydroformylation conditions in the presence of a rhodium carbonylphosphine catalyst complex and various inert solvents such as organic aromatics, aliphatic hydroxylic organic solvents, etc. In both patents, the allyl alcohol conversion was reported to be 99% and 4-hydroxybutanal was typically obtained in 87 wt. % yield. The major by-product was 2-methyl-3-hydroxypropanal (12 wt. %). A rhodium catalyst complexed with special bisphosphine monooxide ligands is taught as catalyzing the hydroformulation of olefinic compounds in the presence of dimethylformamide solvent according to U.S. Pat. No. 4,400,548.

In J. Org. Chem. 45 (1980), 2132, C. U. Pittman, Jr. disclosed the hydroformylation of allyl alcohol to 4-hydroxybutanal and 3-hydroxy-2-methylpropanal using HRh(CO)(PPh$_3$)$_3$ and its polymer-bound analogues. The selectivity of normal/branched products was studied as the function of reaction parameters and ligands employed. The highest normal/branched selectivities were reported with 1,1'-bis(diphenylphosphino)ferrocene at 80%. Benzene and o-xylene solvents were generally used.

In J. of Mol. Cat., Vol. 11, (1981) 233–246, N. A. deMunck reported a heterogeneous gas phase hydroformylation of allyl alcohol using a supported HRh(CO)(PPH$_3$)$_3$ catalyst. A very high selectivity to 4-hydroxybutyraldehyde (97%) was achieved. However, the process is limited to only about 20% allyl alcohol conversion.

Kuraray disclosed the hydroformylation of allyl alcohol using rhodium catalysts in organic solvents such as benzene and toluene and a diphosphinoalkane. The overall n-/iso-ratio of the products were 86.6/13.4, (Kuraray, Japan. Pat. Open. No. 29412/1976, and No. 106407/1979 and Chemical Economy of Engineering Review, Vol. 12, No. 9, 1980). In additional patents (Kuraray, Japan. Pat. Open, No. 84508/1979 and British Patent No. 1,493,154, 1977) to Kuraray, a modified Raney catalyst was claimed for the hydrogenation of hydroxybutyraldehydes into 1,4-butanediol and 3-methyl-1,3-butanediol.

Many of the systems described above lack good conversions of the unsaturated reactant compound and/or good selectivity to the desired product. Further, stability of expensive rhodium catalysts is a problem in many of these processes. It would be an advance in the art if a method could be devised for hydroformulating compounds such as allyl alcohol while simultaneously solving the conversion, selectivity and catalyst stability problems noted above.

SUMMARY OF THE INVENTION

The invention concerns a process for preparing 2-hydroxytetrahydrofuran which comprises hydroformylating allyl alcohol by reaction with carbon monoxide and hydrogen. A rhodium catalyst and a ketone solvent catalyst system are employed.

DESCRIPTION OF THE PREFERRED EMBODIMENTS

In general, the components of the hydroformylation reaction mixture, including the inert solvents, allylically unsaturated compound and rhodium catalyst may be added in any sequence as long as good agitation is employed to provide a good dispersion or a homogeneous reaction mixture. For example, the following represent some variations insofar as the addition of catalyst components, inert solvents and allyl alcohol addition that can be made without departing from the inventive process. These modifications include 1. The catalyst may be preformed and added to the reaction solvents prior to addition of the allyl alcohol and other inert solvent components.

2. Alternatively, to minimize stability problems with the catalyst, the catalyst is formed in situ, usually by mixing the inert solvents and allyl alcohol, followed by the addition of the catalyst components to form the reaction mixture.

3. After using either variation 1 or 2, the deoxygenated catalyst-containing reaction mixture is pressurized with CO and hydrogen and heated until the hydroxy tetrahydrofuran product is formed.

A rhodium catalyst is used in the present invention. Any rhodium-containing compound capable of forming a carbonyl under the reaction conditions can be used. This rhodium compound may be a carbonyl such as hexarhodium hexadecacarbonyl. Preferably, the rhodium carbonyl is complexed with a phosphine ligand. Such catalysts are described in U.S. Pat. Nos. 4,064,145; 4,400,548 and 4,400,549, the pertinent portions of which are incorporated by reference herein. It is especially preferred that the catalyst be a rhodium carbonyl triphenylphosine complex catalyst such as hydridocarbonyltris(triphenylphosphine)rhodium(I). This complex may be written as $HRh(CO)(PPh_3)_3$, where Ph represents a phenyl group. Preferably, an excess of the phosphine ligand is added to provide additional triphenylphosphine.

The method of this invention may be expected to be useful to hydroformylate many kinds of allylically-substituted unsaturated compounds. Suitable allylic compounds include allyl alcohol, alkyl-substituted allylic alcohols, alkyl allylic ethers such as methylallyl ether, ethylallyl ether and allyloctyl ether, as well as allylic esters such as allyl acetate and allyl propionate. It is preferred that the primary reactant is allyl alcohol. When allyl alcohol is employed, the desired product is 2-hydroxytetrahydrofuran.

As noted, a novel feature of the invention is the solvent system. The solvent should be a ketone compound. Useful ketones may contain straight, branched or cyclic alkane groups or aromatic groups. Suitable aliphatic ketones may include methyl isobutyl ketone, 2-decanone, 4-decanone, benzylacetone, di-n-hexyl ketone, 1,3-diphenylacetone, methyl ethyl ketone, acetone and 2,6-dimethyl-4-heptanone, as well as 2-undecanone and 3-undecanone. Suitable aryl ketones include benzophenone, 2-methylbenzophenone, 3-methylbenzophenone as well as related, substituted, benzophenones. Aralkyl ketones that may be suitable in the practice of this invention include n-butyrophenone, acetophenone, ortho, para and meta substituted acetophenones, such as p-ethylacetophenone and o-methoxyacetophenone, as well as phenyl ethyl ketone. Said ketone solvents should be inert with respect to rhodium-catalyzed carbonylation and reduction reactions.

The preferred ketone solvents for rhodium-catalyzed hydroformylation of allylic sybstrates have been found to be either 2-undecanone or acetophenone. It has been surprisingly discovered that the use of these solvent-catalyst combinations increases the allyl alcohol conversion and selectivity to 2-hydroxytetrahydrofuran and also increases the rhodium catalyst stability.

The temperature range which can be employed for hydroformylation is a variable which is dependent upon experimental factors including the particular allylically unsaturated compound employed, the total pressure, the mole ratio of hydrogen and carbon monoxide used, the concentrations of reactants and catalyst, among other things. Using allyl alcohol as the substrate and rhodium carbonyltriphenylphosphine complex as a representative catalyst, an operable range is from about 25° C. to 125° C., or more, when superatmospheric pressures of greater than 100 psig are employed. A narrower range of 50° C. to 120° C. represents the preferred temperature range when the aforementioned allyl alcohol is hydroformylated.

The pressure range which can be employed for hydroformylation is a variable which is also dependent on the factors mentioned above. Using rhodium carbonyltriphenylphosphine as a representative catalyst and allyl alcohol as the substrate, an operable pressure range is from about 100 to 5,000 psig or more, with a mole ratio of $H_2/CO$ being 1:1 when a temperature range of from about 25° C. to 125° C. is employed. A narrower range of from 500 to 1,500 psig represents the preferred pressure range when the narrower temperature range of 50° C. to 125° C. is employed.

The $H_2/CO$ mole ratio may be varied over a range of from 30:1 to 1:30 when suitable temperatures and pressures are employed. A preferred narrower range is from 2:1 to 1:2 of hydrogen/carbon monoxide.

Experimental variables are important in arriving at reaction times. Generally, substantial conversions (90% or higher) of the allyl alcohol to 2-hydroxytetrahydrofuran can almost always be accomplished within 18 hours, with 2 to Experimental work indicates that an initial molar ratio of 10 moles to 10,000 moles of allyl alcohol per mole of rhodium-containing catalyst complex can be employed in most instances. The minimal ratio of 0.0001 moles of catalyst per mole of allyl alcohol is herein referred to as a "catalytic ratio" or "catalytic amount". Much higher ratios (i.e., 25 moles of substrate per mole of rhodium catalyst complex) are not harmful but are economically unattractive. For this reason the favored mole ratio ranges from 50 to 5,000 moles of allyl alcohol per mole of rhodium catalyst complex.

The most particularly preferred combination of reaction conditions include a synthesis gas, carbon monoxide to hydrogen, molar ratio of about 1:1, a molar ratio of rhodium carbonyl-triphenylphosphine complex catalyst to excess triphenylphosphine of about 1:100, a temperature in the range of from about 60° to 80° C. and an operating pressure in the range of about 700 to 900 psi. Again, the ketone solvent should be either acetophenone or 2-undecanone. It was surprisingly discovered that when this unique combination of parameters was used, the selectivity to 2-hydroxytetrahydrofuran is at least 96% and the allyl alcohol conversion is about 100%. Results this good have not been obtained by any previous method.

Allyl alcohol hydroformylation product, 2-hydroxytetrahydrofuran, may be isolated by the usual chemical or physical techniques, such as distillation, solvent extraction, chromatography, etc. Identification is by nuclear magnetic resonance and/or gas-liquid chromatography.

Conversion as defined herein represents the extent of conversion of the reacting allyl alcohol to other products. Conversion is expressed as percentile and is calculated by dividing the amount of allyl alcohol consumed during hydroformylation by the amount of alcohol originally charged and multiplying the quotient by 100. The allyl alcohol conversion in the process of this invention can be at least 90%.

Yield, as defined herein, represents the efficiency in catalyzing the desired hydroformylation reaction relative to other undesired reactions. In this instance hydroformylation to 2-hydroxytetrahydrofuran is the desired conversion. Yield is expressed as a percentile and is calculated by determining the amount of 2-hydroxytetrahydrofuran product formed, divided by the amount of allyl alcohol charged and multiplying the quotient obtained by 100.

Selectivity, as defined herein, is the efficiency in catalyzing a desired hydroformylation reaction relative to the other undesired conversion. Selectivity is expressed as a percentile and is calculated by determining the amount of 2-hydroxytetrahydrofuran product formed, divided by the total amount of aliphatic products formed and multiplying the quotient obtained by 100.

Selectivity can be at least 90% for the inventive process.

Having described the inventive process in general terms, the following examples are submitted to supply specific and illustrative embodiments.

EXPERIMENTAL EXAMPLE A

To a 300 ml stainless steel stirred autoclave were charged $HRh(CO)(PPh_3)_3$ (0.046 g, 0.05 mmole), $Ph_3P$ (1.3 g, 50 mmoles) allyl alcohol (10.0 g, 172 mmoles) and acetophenone (10.0 g). The reactor was purged of air and pressured to 100 psi with a mixture of carbon monoxide and hydrogen at a molar ratio of 1:1 and then heated to 60° C. The pressure was brought to 800 psi and maintained by the addition of carbon monoxide and hydrogen (1:1 molar ratio) from a supply gas cylinder. The aliquot samples were taken through a sample valve at the designated reaction time. After 4 hours, the reaction was stopped and the reactor was allowed to cool to room temperature. The excess gas was vented from the reactor following which 23.3 g light yellow solution was recovered.

Samples of liquid products were analyzed by gas-liquid chromatography and the product selectivities were estimated to be:

| Samples | Allyl Alcohol (conv. %) | 2-hydroxytetrahydrofuran Selectivity % |
|---|---|---|
| 1st (1 hr) | >82 | 96 |
| 2nd (2 hr) | 100 | 96 |
| 3rd (4 hr) | 100 | 96 |

The typical by-product mixtures (at about 4% selectivity) were n-propanol, isobutyraldehyde, methacrolein and n-propanal. The remaining liquid product from the experiment, after completion of the analytical testing, was and the distillates were collected at <50° C. boiling point.

The residual catalyst solid (pale yellow, 1.5 g) was then dissolved and combined with fresh allyl alcohol (10.0 g) and acetophenone (10.0 g) and charged to the autoclave. The identical experimental procedures were repeated in the second catalyst cycle, the following results obtained:

| Sample | Allyl Alcohol (conv. %) | 2-hydroxytetrahydrofuran Selectivity % |
|---|---|---|
| 1st (1 hr) | 70 | >96 |
| 2nd (2 hr) | 93 | >96 |
| 3rd (4 hr) | >96 | >96 |

In the third catalyst cycle under the above reaction conditions the results were:

| Sample | Allyl Alcohol (conv. %) | 2-hydroxytetrahydrofuran Selectivity % |
|---|---|---|
| 1st (1 hr) | 69 | >96 |
| 2nd (2 hr) | 93 | >96 |
| 3rd (4 hr) | 96 | >96 |

Thus, the stability of the catalyst in a recycle mode was confirmed.

EXAMPLES B–E

In these studies on the hydroformylation of allyl alcohol catalyzed by $HRh(CO)(PPh_3)_3$, the purpose is to focus on determining the effect of solvent structure upon allyl alcohol conversion, selectivity to 2-hydroxytetrahydrofuran and catalyst stability. The experimental procedure is that of Example A. The allyl alcohol charge at the beginning of each run was 10.0 g, the quantities of rhodium catalyst, phosphine ligand and added solvent are given in Table I.

TABLE I

| | | | | | | | | Selectivities (A %) | | |
|---|---|---|---|---|---|---|---|---|---|---|
| Example | Catalyst | Ligand | Solvent | Syngas Ratio, (CO/H$_2$) | Conditions | Liq- Recovery, (g) | Allyl Alcohol Conv. (%) | 2-hydroxy-tetrahydro-furan | 1,4-Butane-diol | C$_3^-$ By-product |
| B | HRh(CO)(PPh$_3$)$_3$ (0.046 g) | Ph$_3$P (1.3 g) | None | 1:2 | 800 psi 69–82° C. 5 hrs | 11.7 | 85 | 31 | 0 | 24 |
| C | HRh(CO)(PPh$_3$)$_3$ (0.046 g) | Ph$_3$P (1.3 g) | 2-undecanone (10 g) | 1:2 | 800 psi 73–83° C. 4 hrs. | 24.7 | >95 | 68 | 0 | 32 |
| D | HRh(CO)(PPh$_3$)$_3$ (0.046 g) | Ph$_3$P (1.3 g) | 2-undecanone (10 g) + 1,4-butanediol (7.7 g) | 1:2 | 800 psi 77–80° C. 5 hrs. | 30.8 | >95 | 60 | — | 40 |
| E | HRh(CO)(PPh$_3$)$_3$ (0.046 g) | Ph$_3$P (1.3 g) | 2-undecanone | 1:1 | 800 psi 60° C. 1 hr. | — | 86 | 92 | 0 | 4 |

A number of observations may be made about these experimental runs. For example, a comparison of Examples B and C reveals that the addition of 2-undecanone solvent increases the allyl alcohol conversion and selectivity to 2-hydroxytetrahydrofuran. Comparison of Examples C and E teaches that the selectivity to 2-hydroxytetrahydrofuran is sensitive to the composition of the synthesis gas feed; a molar ratio of Co to H$_2$ of 1:1 is preferred (see Example E). In Example D, the addition of 1,4-butanediol to the feed mixture does not seriously inhibit the formation of 2-hydroxytetrahydrofuran.

At the optimal reaction conditions of 800 psi, a CO/H$_2$ molar ratio of 1:1, 60° C., reaction time of 2 to 4 hours and using a HRh(CO)(PPh$_3$)$_3$/Ph$_3$P molar ratio of 1:100 in ketone T solvents, a 96% selectivity to 2-hydroxytetrahydrofuran and a 100% allyl alcohol conversion is achieved; e.g., Example A.

EXAMPLE F

Catalyst Recycles in Various Solvents

Reaction Conditions: CO/H$_2$=1:2; 800 psi; 2 hours, 60° C.

Catalyst: HRh(CO)(PPh$_3$)$_3$ (0.092 g) and triphenylphosphine (2.6 g)

Materials Charged: Allyl alcohol (20 g) and solvent (20 g)

TABLE II

| | Conversion of Allyl Alcohol (%) | | |
|---|---|---|---|
| Cycles | in 2-undecanone | p-xylene | n-Pr$_3$N |
| 1st | >55 | >50 | >95 |
| 2nd | 100 | 90 | 55 |
| 3rd | 100 | 57 | 54 |

EXAMPLE G

Catalyst Recycles in Various Solvents

Reaction Conditions: CO/H$_2$=1:1; 800 psi; 60° C.

Catalyst: HRh(CO)(PPh$_3$)$_3$ (0.046 g) and triphenylphosphine (1.3 g)

Materials Charged: Allyl alcohol (10.0 g) and solvent (10.0 g)

TABLE III

| | | in p-xylene | | in acetophenone | |
|---|---|---|---|---|---|
| Cycles | Sample Time | Conversion, % | Selectivities, % | Conversion, % | Selectivities, % |
| I | 2 hrs. | 100 | 94 | 100 | 96 |
| II | 2 hrs. | 88 | >96 | >93 | >96 |
| | 4 hrs. | 100 | 96 | 100 | 96 |
| III | 2 hrs. | 89 | >96 | 93 | >96 |
| | 4 hrs. | 100 | 96 | 100 | 96 |

Comparative results presented in Tables II and III show the importance of solvent structure respect to the stability of the rhodium catalysts. Acetophenone and 2-undecanone are found to be superior. It is interesting to note that the residue of each distillation contained no significant amount of heavy materials, indicating the stability of 2-hydroxytetrahydrofuran during distillation.

Many modifications may be made by one skilled in the art without departing from the spirit and scope of the invention which are defined only by the appended claims. For example, solvents, proportions and reaction conditions could be changed to optimize the yield to 2-hydroxytetrahydrofuran.

We claim:

1. A process for preparing 2-hydroxytetrahydrofuran which comprises hydroformylating allyl alcohol by reaction with carbon monoxide and hydrogen in the presence of a rhodium carbonyl catalyst and a ketone solvent.

2. The process of claim 1 in which the ketone solvent is selected from the group consisting of methyl isobutyl ketone, 2-decanone, 4-decanone, benzylacetone, di-n-hexyl ketone, 1,3-diphenylacetone, methyl ethyl ketone, acetone, 2,6-dimethyl-4-heptanone, 2-undecanone, 3-undecanone, benzophenone, 2-methylbenzophenone, 3-methylbenzophenone, n-butyrophenone, acetophenone, p-ethylacetophenone, o-methoxyacetophenone, phenyl ethyl ketone and mixtures thereof.

3. The process of claim 1 in which the ketone solvent is selected from the group consisting of acetophenone and 2-undecanone.

4. The process of claim 1 in which the reaction is conducted at a temperature in the range of from about 50° to 120° C. and at a pressure in the range from about 500 to 1,500 psi.

5. The process of claim 1 in which the catalyst is a rhodium carbonyl-triphenylphosphine complex together with excess triphenylphosphine.

6. The process of claim 1 in which the rhodium carbonyl catalyst is hydridocarbonyltris(triphenylphosphine) rhodium(I) in the presence of excess triphenylphosphine.

7. A process for preparing 2-hydroxytetrahydrofuran which comprises hydroformylating allyl alcohol by reaction with carbon monoxide and hydrogen in the presence of a rhodium carbonyl catalyst and a ketone solvent selected from the group consisting of acetophenone and 2-undecanone, at a temperature in the range of from about 50° to 120° C. and at a pressure in the range from about 500 to 1,500 psi.

8. The process of claim 7 in which the catalyst is a rhodium carbonyl-triphenylphosphine complex together with excess triphenylphosphine.

9. The process of claim 7 in which the rhodium carbonyl catalyst is hydridocarbonyltris(triphenylphosphine) rhodium(I) in the presence of excess triphenylphosphine.

10. A process for preparing 2-hydroxytetrahydrofuran in at least 96% selectivity which comprises hydroformylating allyl alcohol, at about 100% conversion, by reaction 1:1 in the presence of a rhodium carbonyl-triphenylphosphine complex catalyst together with excess triphenylphosphine at a molar ratio of about 1:100, and a ketone solvent selected from the group consisting of acetophenone and 2-undecanone, at a temperature in the range of from about 50° to 80° C. and at a pressure in the range from about 700 to 900 psi.

11. The process of claim 10 in which the rhodium carbonyl catalyst is hydridocarbonyltris(triphenylphosphine) rhodium(I) in the presence of excess triphenylphosphine.

* * * * *